US010202432B2

(12) United States Patent
Chang et al.

(10) Patent No.: US 10,202,432 B2
(45) Date of Patent: Feb. 12, 2019

(54) DUAL TARGETING DRUG CARRIER AND APPLICATION THEREOF

(71) Applicant: National Yang-Ming Univeristy, Taipei (TW)

(72) Inventors: Cheng Allen Chang, Taipei (TW); Keng-Li Lan, Taipei (TW); Hsin-Ell Wang, Taipei (TW); Shun-Fu Chang, Puzi (TW); Jia-Je Li, Taipei (TW); Pei-Chia Chan, New Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 0 days.

(21) Appl. No.: 14/953,172

(22) Filed: Nov. 27, 2015

(65) Prior Publication Data

US 2017/0058011 A1 Mar. 2, 2017

(30) Foreign Application Priority Data

Aug. 27, 2015 (TW) ............................. 104128165 A

(51) Int. Cl.

| | |
|---|---|
| ***C07K 14/485*** | (2006.01) |
| ***C07K 5/08*** | (2006.01) |
| ***A61K 38/00*** | (2006.01) |
| ***C07K 5/09*** | (2006.01) |
| ***C07K 14/52*** | (2006.01) |

(52) U.S. Cl.

CPC .......... *C07K 14/485* (2013.01); *C07K 5/0817* (2013.01); *C07K 14/52* (2013.01); *A61K 38/00* (2013.01); *C07K 2319/01* (2013.01)

(58) Field of Classification Search

None

See application file for complete search history.

(56) References Cited

U.S. PATENT DOCUMENTS

| | | | | |
|---|---|---|---|---|
| 5,196,510 A * | 3/1993 | Rodwell | .......... A61K 47/48238 | 436/545 |
| 2007/0258889 A1* | 11/2007 | Douglas | ............... A61K 9/5184 | 424/1.37 |
| 2008/0181852 A1* | 7/2008 | Yu | ...................... A61K 49/0056 | 424/9.36 |
| 2010/0310506 A1* | 12/2010 | Corti | .................... C07K 14/525 | 424/85.2 |

FOREIGN PATENT DOCUMENTS

| | | | |
|---|---|---|---|
| CN | 101284877 | * 10/2008 | .............. Y02P 20/52 |
| CN | 102234679 | * 11/2011 | ............... C12Q 1/04 |
| WO | WO2010083495 | * 7/2010 | ............ A61K 38/18 |

OTHER PUBLICATIONS

Curnis et al. Coupling Tumor Necrosis Factor-α with αV integrin ligands improves its antineoplastic activity. Cancer Res. 64, 565-571, 2004.*
Vella et al. A recombinant chimeric Epidermal Growth Factor-like module with high binding affinity for integrins, J. Biol. Chem., 278, 19834-19843, 2003.*
Chen et al. Fusion protein linkers: Property, design and functionality, Adv. Drug Del. Rev., 65, 1357-1369, 2013.*
English transaltion of CN101284877 (May 20, 2017).*
English Translation of CN102234679 (May 20, 2017).*
Seliktar et al., MMP-2 sensitive, VEGF-bearing bioactive hydrogels for promotion of vascular healing, J. Biomed. Mater. Res. 68A, 704-716, 2004.*

* cited by examiner

*Primary Examiner* — Elly-Gerald Stoica
(74) *Attorney, Agent, or Firm* — Muncy, Geissler, Olds & Lowe, P.C.

(57) ABSTRACT

A dual targeting drug carrier is provided. The dual targeting drug carrier comprises a first targeting molecule and a second targeting molecule, wherein the targeting molecule comprises peptide, protein or antibody. The targeting molecule can bind to specific receptors, proteins, or glycoproteins to recognize the specific tumor cells, tissues, or organs. The dual targeting drug carriers are further conjugated with imaging agents, radioactive molecules (radiopharmaceuticals, isotopes, or chemotherapeutic drugs) or nanoparticles to form a conjugate.

5 Claims, 8 Drawing Sheets
(2 of 8 Drawing Sheet(s) Filed in Color)

Specification includes a Sequence Listing.

A

| Protein | Concen tration | Volume (ml) | Total weight (mg) |
|---|---|---|---|
| hEGF | 0.67 | 7.5 | 5.03 |
| YNGRT-hEGF | 0.56 | 8 | 4.46 |
| RGD-hEGF | 1.01 | 6 | 6.06 |
| RGD4C-hEGF | 0.29 | 6 | 1.74 |

B

DUAL TARGETING DRUG CARRIER AND APPLICATION THEREOF

CROSS-REFERENCE TO RELATED APPLICATIONS

This Non-provisional application claims priority under 35 U.S.C. § 119(a) on Patent Application No(s). 10412865 filed in Taiwan, Republic of China Aug 27, 2015, the entire contents of which are hereby incorporated by reference.

FIELD OF THE INVENTION

The present invention relates to a novel targeting fusion protein, and in particular relates to a dual targeting drug carrier including two targeting molecules.

BACKGROUND OF THE INVENTION

Cancer/tumor is a major cause of morbidity in the United States, and the mortality rate of several cancer types is increasing. Cancer cells share the characteristics of disordered control over normal cell division, growth, and differentiation. The initial clinical manifestations of tumor are extremely heterogeneous, with over 70 types of cancer occurring in virtually every organ and tissue of the body. Some of those classified cancer types may represent different molecular diseases. Unfortunately, some cancers may be asymptomatic until late in the disease course, when treatment is more difficult, and prognosis is considerately poor.

Treatments for cancer typically includes surgery, chemotherapy, and/or radiation therapy. Although nearly 50 percent of cancer patients can be effectively treated using these methods, serious side effects that diminished quality of life are arisen from current therapies. Most chemotherapeutic drugs act on both normal and cancerous tissues. One of the challenges in treating cancerous tumors with chemotherapy is maximizing the killing of cancer cells while minimizing the healthy tissue damage. Depending on the administration route (e.g., intravenous) and nature of the drug (e.g., its chemical and pharmacokinetic properties), only a small fraction of the dose reaches the target cells; the remaining drug acts on other tissues or is rapidly eliminated.

To improve delivery efficiency and reduce toxicity to non-target cells, various strategies have been used to deliver drugs to specific sites in the human body. For example, the use of a toxin-conjugated monoclonal antibody in cancer treatment has been reported. The antibody provides selectivity for the aimed target, but there still remains the problem of interaction with non-target cells during the route to the intended site of action.

Currently, in order to develop novel targeting drugs, it is very important to find a biomarker of the tumor angiogenesis system. Various specific membrane proteins of the tumor angiogenesis system are highly expressed, such as integrin $\alpha v\beta 3$, $\alpha v\beta 5$ and vascular endothelial growth factor receptor 2. Additionally, it is well-known that the Arg-Gly-Asp (RGD) or Asn-Gly-Arg (NGR) peptides can specifically bind to tumor angiogenic endothelial cells.

However, tumor cells are highly variable, and the treated cancer cells become resistant to the treatment quickly. The current drugs and diagnosis agents for improving survival of cancer patients are ineffective.

SUMMARY OF THE INVENTION

In view of the above-mentioned problems, the present invention provides a novel catTier for the cancer diagnosis and treatment. The dual targeting drug carrier of the present invention is a fusion protein platform and can decrease the barrier and costs of pharmaceuticals.

The invention provides a dual targeting drug carrier comprising a first targeting molecule and a second targeting molecule.

In one embodiment, the first and second targeting molecules are peptide or protein.

In one embodiment, the first and second targeting molecule are specifically bound to tumor cells and/or vascular endothelial cells in tumor microenvironment.

In one embodiment, the first and second targeting molecule comprise small peptides and/or proteins. Small peptides include, but not limited to Arg-Gly-Asp (RGD), Asn-Gly-Arg (NGR), cyclic NGR, disulfide-based cyclic RGD (iRGD), Lyp-1, gastrin, bombesin, octreotide, or derivatives thereof. Proteins include, but not limited to epidermal growth factor (EGF), anti-EGFR antibody, vascular endothelial growth factor (VEGF), anti-VEGFR antibody, anti-HER2 antibody, hepatocyte growth factor receptor (HGFR), anti-HGFR antibody, tumor necrosis factor (TNF), or anti-TNF antibody.

In one embodiment, the first targeting molecule is linked to the second targeting molecule.

In one embodiment, the linker is a peptide of 5 to 20 amino acids.

In one embodiment, the linker comprises GG, PGGGG, or GGGGSGGGGS.

In one embodiment, the dual targeting drug carrier further comprises a radioisotope.

The present invention also provides a pharmaceutical composition comprising the dual targeting drug carrier and a pharmaceutically accepted carrier.

In one embodiment, the pharmaceutical composition further comprises a liposome.

In one embodiment, the pharmaceutical composition further comprises a nanoparticle.

Detailed description of the invention is given in the following embodiments with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 5A, M is a molecule weight marker, C is control group (without protein), E is EGF group (25 nM), R-E is RGD-EGF (25 nM), and R4C-E is RGD4C-EGF (25 nM). In FIG. 5B, M is a molecule marker, C is control group (without protein), R-V is RGD-VEGF, and R4-V is RGD4C-VEGF.

DETAILED DESCRIPTION OF THE INVENTION

Figure 1:
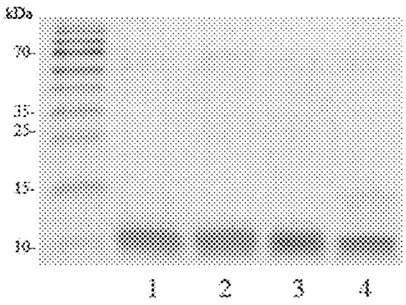
FIG. 1 illustrates a SDS-PAGE result of VEGF, RGD-VEGF, RGD4C-VEGF, EGF, RGD-EGF, and RGD4C-EGF. The lane M is a molecular weight marker. Lane 1 is VEGF (15.3 Da). Lane 2 is RGD-VEGF (15.6 Da). Lane 3 is RGD4C-VEGF (16.3 Da).
Figure 1:
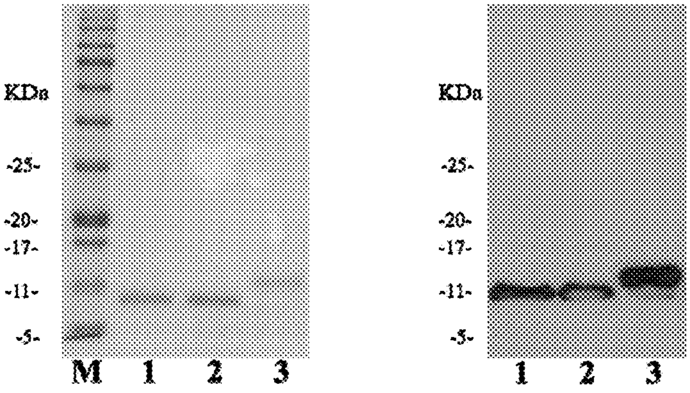
Figure 2A:
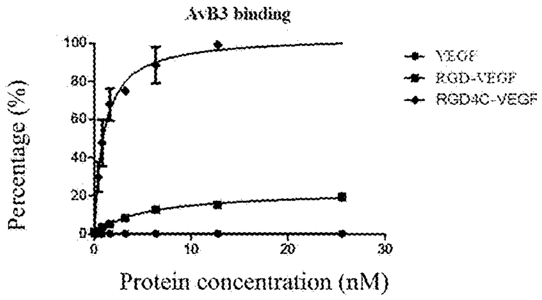
FIGS. 2A-2F are graphs showing the binding of "RGD-VEGF or RGD4C-VEGF" and "$\alpha v\beta 3$, VEGFR1, or VEGFR2". RGD-EGF and RGD4C-EGF can bind to both integrin $\alpha v\beta 3$ and EGFR.
Figure 2B:
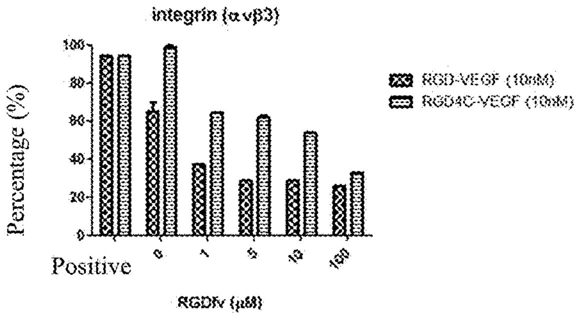
Figure 2C:
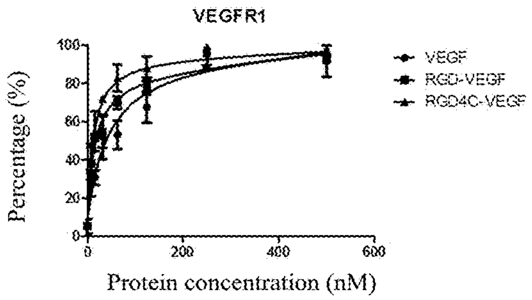
Figure 2D:
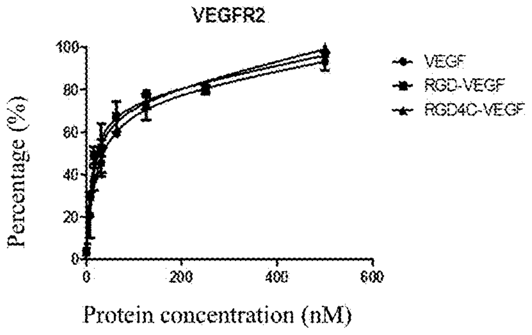
Figure 2E:
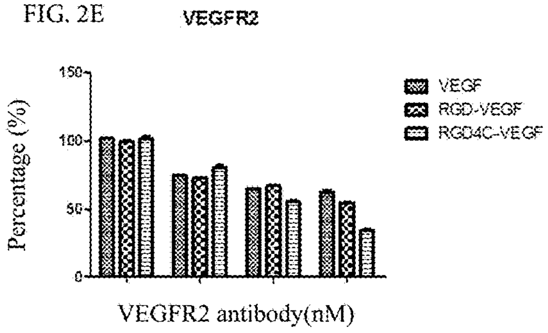
Figure 2F:
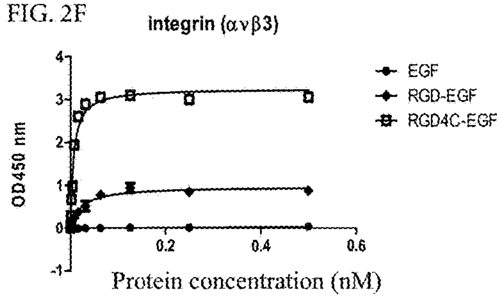
Figure 3A:
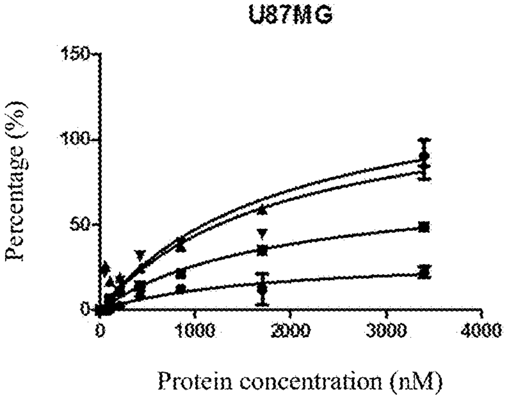
FIGS. 3A-3B are graphs showing the binding of RGD-EGF and RGD4C-EGF to U87MG cells (the integrin $\alpha v\beta 3$ and EGFR are expressed). RGD-VEGF and RGD4C-VEGF can bind to the cells expressing integrin $\alpha v\beta 3$ and EGFR.
Figure 3B:
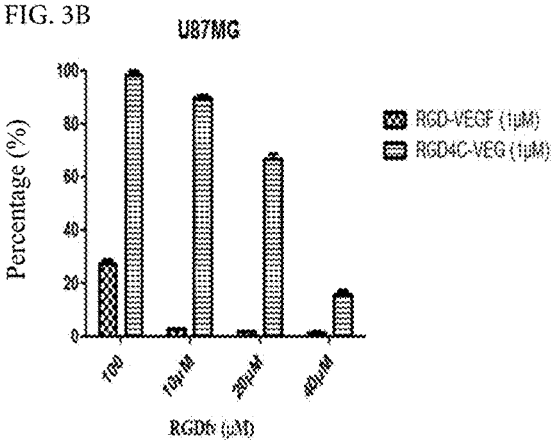
Figure 3C:
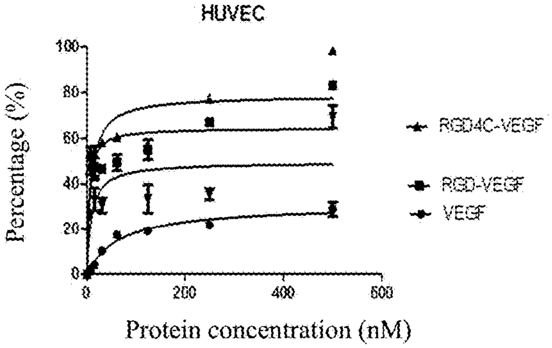
FIGS. 3C-3D are graphs showing the binding of RGD-VEGF, RGD4C-VEGF, and NGR-VEGF to HUVEC cells. RGD-VEGF, RGD4C-VEGF, and NGR-VEGF can bind to the cells expressing VEGFR1, VEGFR2, and integrin $\alpha v\beta 3$.
Figure 3D:
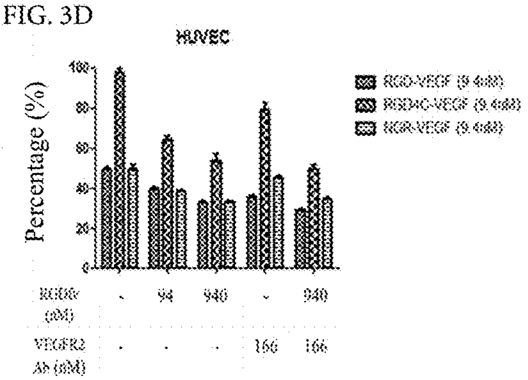

The present disclosure is directed to a novel targeting fusion protein. One aspect of the present disclosure relates to fusion proteins of the invention, radio-labeled fusion proteins and methods for producing the fusion proteins of the invention.

The following description is of the best-contemplated mode to carry out the invention. This description is for purpose of illustrating the general principles of the invention and should not be taken in a limiting sense. The scope of the invention is best determined by reference to the appended claims.

The section headings used herein are for organizational purposes only and are not to be construed as the limiting subject matter described. All references or portions of references cited in this application are expressly incorporated by reference herein in their entirety for any purpose.

The present invention provides a dual targeting drug carrier comprising a first targeting molecule and a second targeting molecule.

The term "targeting molecule" refers to a peptide, antibody, or protein. The targeting molecule of the present invention can be chemically modified to increase their stability. A chemically modified peptide or a peptide analog includes any functional chemical equivalent of the peptide characterized by its increased stability and/or efficacy in vivo and in vitro. The term "peptide analog" also refers to any amino acid derivative of a peptide as described herein. A peptide analog can be produced by procedures that include, but are not limited to, modifications to side chains.

The targeting molecules described herein can bind to lesions, particularly tumor, cancer tissues/cells and vascular endothelial cells in tumor microenvironment, both in vitro and in vivo. Thus, when targeting molecules conjugated with a reporting agent (e.g., a fluorescent or radioactive agent in bioimaging), they direct the agent to a cancer site, thereby facilitating cancer diagnosis. As used in this disclosure, "conjugated" means two entities (e.g., a tumor targeting peptide and a reporting agent) are associated with sufficient affinity that the therapeutic/diagnostic benefit of the association between the two entities is realized. Conjugation can be achieved by covalent or non-covalent bonding, as well as by other forms of association, such as entrapment of one entity on or within the other.

The targeting molecules can be a small peptide and/or protein. The small peptide includes, but is not limited to, Arg-Gly-Asp (RGD), Asn-Gly-Arg (NGR), cyclic NOR, disulfide-based cyclic RGD (iRGD), Lyp-1, gastrin, bombesin, octreotide, or derivate thereof. The protein includes, but is not limited to, epidermal growth factor (EGF), anti-EGFR antibody, Vascular endothelial growth factor (VEGF), anti-VEGFR antibody, anti-HER2 antibody, hepatocyte growth factor receptor (HGFR), anti-HGFR antibody, Tumor necrosis factor (TNF), or anti-TNF antibody.

In one embodiment, the targeting molecules can be conjugated with a bioimaging molecule(s) or radio radiotherapeutic agent(s) (radioactive nuclide, radiopharmaceuticals, or isotope) to form a conjugate.

Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, or $^{67}$Ga.

Exemplary radiopharmaceuticals suitable for in vivo imaging include $^{111}$In Oxyquinoline, $^{131}$I Sodium iodide, $^{99m}$Tc Mebrofenin, and $^{99m}$Tc Red Blood Cells, $^{123}$I Sodium iodide, $^{99m}$Tc Exametazime, $^{99m}$Tc Macroaggregate Albumin, $^{99m}$Tc Medronate, $^{99m}$Tc Mertiatide, $^{99m}$Tc Oxidronate, $^{99m}$Tc Pentetate, $^{99m}$Tc Pertechnetate,$^{99m}$Tc Sestamibi, $^{99m}$Tc Sulfur Colloid, $^{99m}$Te Tetrofosm in, Thallium-201, or Xenon-133.

Isotope include, but are not limited to, $^{52}$Fe, $^{52}$mMn, $^{55}$Co, $^{64}$Cu, $^{67}$Ga, $^{68}$Ga, $^{99}$mTc, $^{111}$In, $^{123}$I, $^{125}$I, $^{131}$I, $^{32}$P, $^{47}$Sc, $^{67}$Cu, $^{90}$Y, $^{109}$Pd, $^{111}$Ag, $^{149}$Pm, $^{186}$Re, $^{188}$Re, $^{211}$At, $^{212}$Bi, $^{213}$Bi, $^{105}$Rh, $^{153}$Sm, $^{177}$Lu, or $^{198}$Au.

The targeting molecules can be conjugated with the radioactive nuclide by a metal chelator. The radioactive nuclide comprises DTPA, NOTA, DOTA, or derivative thereof.

The tumor targeting peptide or conjugate thereof can be administered parenterally, topically, rectally, nasally, buccally, vaginally, via an implanted reservoir, or via inhalation spray. The term "parenteral" as used herein includes subcutaneous, intracutaneous, intravenous, intramuscular, intraarticular, intraarterial, intrasynovial, intrastemal, intrathecal, intralesional, and intracranial injection or infusion techniques.

The term "linker peptide" refers to a sequence containing 2-50, preferably, 5-20 synthetic amino acids that connect or link two polypeptide sequences, e.g., that link two polypeptide domains. The linker of the present invention connects a first moiety to a second moiety in a linear sequence. In one embodiment, a the flexible steric linker may be selected from the group consisting of (GGGGS)n, (G)n, (EAAAK)n, (XP)n or (PAPAP)n. such as GG, GGSG, GGGS, PGGGG, GGGGS, GGSGG, GGGSGG, GGGSGGG, GGGSGGGS, GGGSGGGGS, ASGG, GGGSASGG, SGCGS, GGGGSGGGG, GGGGSGGGGS, GGSHG, SGGCGGS, or AACAA.

As mentioned above, the dual targeting drug carrier can be used a tumor targeting drug carrier to carry the tumor drugs or others. Further, the dual targeting drug carrier also can be used a molecule image probe for tumor diagnosis to carry bioimaging molecules. The dual targeting drug also has the effect of cancer diagnosis.

EXAMPLE 1

Construction of Fusion Protein Vector

DNA fragments of EGF (SEQ ID NO: 11), RGD-EGF (SEQ ID NO: 12), RGD4C-EGF (SEQ ID NO: 13), VEGF (SEQ ID NO: 16), RGD-VEGF (SEQ ID NO: 17), and RGD4C-VEGF (SEQ ID NO: 18) were ligated into Nco I and Xho I sites of pET28a (+) vectors, respectively. The C-terminus of RGD or RGD4C was linked to N-terminus of EGF or VEGF, and the DNA fragment of RGD-EGF, RGD4C-EGF, RGD-VEGF, and RGD4C-VEGF included a linker (GG). The obtained pET28a(+) EGF, RGD-EGF, RGD4C-EGF, VEGF, RGD-VEGF, and RGD4C-VEGF vectors were transformed into *E. coli* DH5α to preserve vector DNA. The sequences of vectors were confirmed by DNA sequencing.

EXAMPLE 2

Expression and Purification of the Targeting Fusion Proteins

Vectors prepared in Example 1 were transformed into *E. coli* BL21 (DE3) using traditional CaCl2 method and then selected by 50 μg/mL kanamycin. The liquid culture of *E. coli* BL21 (DE3) stains containing protein expression vectors were induced by 1 mM IPTG at 37° C. for 16 hours. Bacterial cells were lysed using French press at 30 PSI, and then centrifuged by 13,000 for 30 minutes. Supernatants and pellets were collected and analyzed by sodium dodecyl sulfate polyacrylamide gel electrophoresis (SDS-PAGE) to examine the expression of the targeting fusion proteins. If the proteins were accumulated in inclusion bodies of bacteria, the targeting proteins were dissolved, filtrated by filter membrane with pore sizes of 0.45 μm, diluted the filtrated sample in 50 fold volume of refolding buffer (20 mM Tris, 0.1 Mm GSSG, 1 mM GSH, and 1 mM EDTA, pH 8.0) for protein refolding at 4° C. for 12 hours, and the concentration of targeting proteins was not higher than 0.2 mg/mL after dilution in refolding buffer. The precipitates were removed by filter membrane with pore sizes of 0.45 μm.

The refolding buffer was applied to a nickel column at a flow rate of 5 mL/min, and then the nickel column was washed with Buffer A (20 mM Tris (pH8.0), 500 mM NaCl, 20 mM imidazole, and 0.5 mM PMSF). The bound recombinant fusion protein was eluted with a buffer with various concentration of imidazole. The concentration of imidazole was adjusted by Buffer A and Buffer B (20 mM Tris (pH8.0), 500 mM NaCl, 500 mM imidazole, and 0.5 mM PMSF). The eluate was purified by a gel column (HiPrap™ 26/60 S-100) to remove remaining impurities. The purified proteins were concentrated by Amicon® Ultra Centrifugal Filters (Millipore), and the concentration was adjusted to 0.5-3 mg/mL. The proteins were dispensed into microcentrifuge tubes and stored at −80° C. As shown in FIG. 1, the protein purity was analyzed by SDS-PAGE.

EXAMPLE 3

Receptor Binding Assay 3.1 Binding of Targeting Fusion Protein to Integrin

ELISA cell binding assays were used in this Example to analyze the binding of targeting fusion proteins [EGF (SEQ ID NO: 1), RGD-EGF (SEQ ID NO: 2), NGR-EGF, RGD4C-EGF (SEQ ID NO: 3), VEGF (SEQ ID NO: 6), RGD-VEGF (SEQ ID NO: 7), NGR-VEGF, and RGD4C-VEGF (SEQ ID NO: 8)) and cells. 96-wells ELISA plates were coated with 25 μg/well of Integrin (αvβ3) dissolved in PBS buffer (containing calcium and magnesium ions) at 4° C. for 12 hours, and then blocked with 3% BSA at 25° C. for 1 hour. The diluted targeting fusion proteins were added and cultured at 25° C. for 2 hours. After washed with PBS buffer (containing calcium and magnesium ions), mouse anti-His HRP conjugated antibodies were added to detect the bound proteins to integrin. The optical density (OD) at a wavelength of 450 nm was measured to quantify how many proteins were bound to the receptors. The obtained values were analyzed by prism software to obtain a nonlinear curve fitting. According to curve fitting results, the Kd value were measured.

3.2 Binding of Targeting Fusion Protein to EGFR or VEGFR 96-well ELISA plates were coated with 25 μg/well of anti-IgG antibodies dissolved in PBS buffer (containing calcium and magnesium ions) at 4° C. for 12 hours, and then blocked with 3% BSA at 25° C. for 1 hour. 25 ng/well of EGFR or VEGFR was added and cultured at 25° C. for 2 hours. After washed with PBS buffer (containing calcium and magnesium ions), mouse anti-His HRP conjugated antibody was added to detect the bound proteins to receptors. The optical density (OD) at a wavelength of 450 nm was measured to quantify how many proteins were bound to the receptors. The obtained values were analyzed by prism software to obtain a nonlinear curve fitting. According to curve fitting results, the Kd value were measured to verify the relative binding affinities of each recombinant protein to its owned receptors.

The Kd value of EGF, RGD-EGF or RGD4C-EGF to EGFR was 2.38, 20.35 and 14.33 nM, respectively. The Kd value of VEGF, RGD-VEGF or RGD4C-VEGF to Integrin was 0, 5.0 and 1.0, respectively. The Kd value of VEGF, RGD-VEGF or RGD4C-VEGF to VEGFR1 was 15.3, 11.3 and 11.4, respectively. The Kd value of VEGF, RGD-VEGF or RGD4C-VEGF to VEGFR2 was 22.2, 12.1 and 13.9, respectively.

As shown in FIGS. 2A-2F, the dual targeting fusion proteins can bind to at least two different receptors and have dual-targeting activity. RGD-EGF and RGD4C-EGF can bind to Integrin (αvβ3) and EGFR, respectively. RGD-VEGF and RGD4C-VEGF can bind to Integrin (αvβ3), VEGFR1 and VEGFR2, respectively.

EXAMPLE 4

Cell Binding Assay

MDA-MB468 (high EGFR expression), MDA-MB231 (Moderate EGFR expression), MCF-7 (low expression), HT1080 (APN expression), U87MG (αvβ3 expression), and HUVEC (VEGFR and αvβ33 expression) cells were used in this Example to analyze the specific binding affinity of the dual targeting fusion proteins and various receptors.

20,000 cells/well of MDA-MB468, MDA-MB231, MCF-7, HT1080, U87MG, and HUVEC cells were seeded into 96-well plates, and cultured at 37° C. for 12 hours. When cells were attached to plates, pre-cooled 4% para-formadehyde was added to fix cells at room temperate for 15 minutes. Fixed cells were cultured with 3% FBS at 25° C. for 1 hour, and then serially diluted targeting fusion proteins were added and cultured at 25° C. for 1 hour. After washed with PBS buffer (containing 1 mmol/L CaCl2 and 0.5 mmol/L MgCl2), mouse anti-His HRP conjugated antibodies were added and followed by the addition of a 3,3',5,5'-Tetramethylbenzidine (TMB) to detect the bound proteins to cell surface receptors. The optical density (OD) at a wavelength of 450 nm was measured to quantify how many proteins were bound. The obtained values were analyzed by prism software to obtain a nonlinear curve fitting and Kd value.

The Kd value of EGF, RGD-EGF, and RGD4C-EGF to EGFR on MDA MB 468 cells was 16.38, 26.97 and 22.22 nM, respectively. The Kd value of VEGF, RGD-VEGFD4C-VEGF, NGR-VEGF to intergrin on U87MG cells was 1.74, 1.83, 1.9 and 1.9 μM, respectively. The Kd value of VEGF, RGD-VEGF, RGD4C-VEGF, NGR-VEGF to VEGFR or intergrin on HUVEC cells was 12.7, 11.9, 6.4 and 9.4 nM, respectively.

As shown in FIG. 3, RGD-EGF, RGD4C-EGF, RGD-VEGF, and RGD4C-VEGF could bind to the cells expressing the corresponding receptors, respectively.

Competitive binding assays of the RGD peptide or VEGFR antibody to RGD-VEGF and RGD4C-VEGF in U87MG or HUVEC cells were conducted. The addition of the competitor, the anti-VEGF antibodies herein, could effectively decrease the binding of RGD-VEGF or RGD4C-VEGF to cells. The results indicated that the dual targeting proteins could specifically bind to cancer biomarkers.

EXAMPLE 5

Cell Adhesion Assay

Extracellular matrix (ECM) cell adhesion assay was used in this Example to analyze the cell adhesive properties. 96-well plates were coated with targeting fusion proteins with various concentrations at 16° C. for 1 hour. After coating, 3%BSA was added at 25° C. for 1 hour. The cancer cells (U87MG, 5×105 cells/well) were starved for 1 hour and then added to 96-well plates. After 2 hours incubation at 37° C., the cells were washed with D-PBS to remove unbound cells. Finally, MTT was added and cultured at 37° C. for 1 hour. MTT agent was reduced to formazan (dark-blue crystals) by cells. Foimazan crystals were dissolved by DMSO to detect the optical density (OD) at a wavelength of 570 nm. The cell adhesion was measured by following equation:

Cell adhesion (%)=(OD value of experimental group/OD value of control group)×100%

Figure 4A:
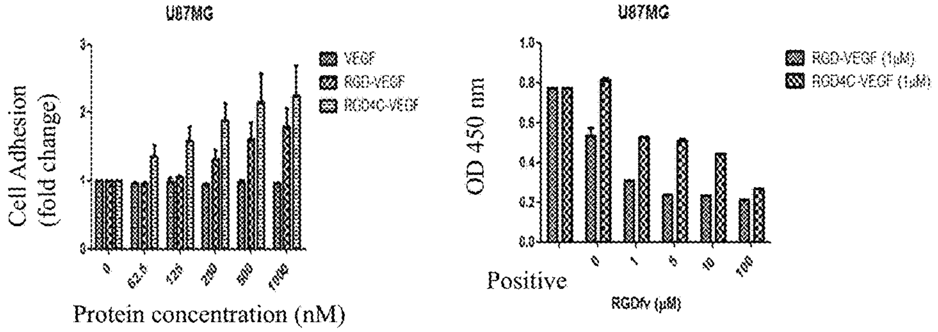
FIGS. 4A-4B illustrate the results of cell adhesion assay. RGD-VEGF and RGD4C-VEGF coated plates can increase the cells adhesion ability of U87MG and HUVEC cells. The cell adhesion was decreased when high concentration RGD peptide was added as a competitor.
Figure 4B:
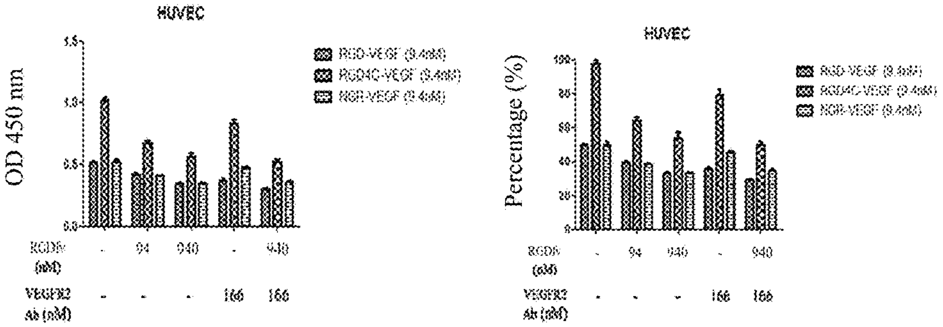

According to FIGS. 4A and 4B, RGD-VEGF and RGD4C-VEGF increased the U87MG and HUVC cells on the plates. However, the cell adhesion was suppressed when excess amount of RGD peptide was added for binding competition.

EXAMPLE 6

Cell Activation Assay

Cell-based assays were used to determine the activation of cell signaling by fusion proteins. Human tumor cells were cultured with 25 nM targeting fusion protein at 37° C. for 60 minutes, and then protein extract of cells was collected for western blot analysis to analyze the phosphorylation of cell receptors and their downstream signal molecules.

Figure 5A:
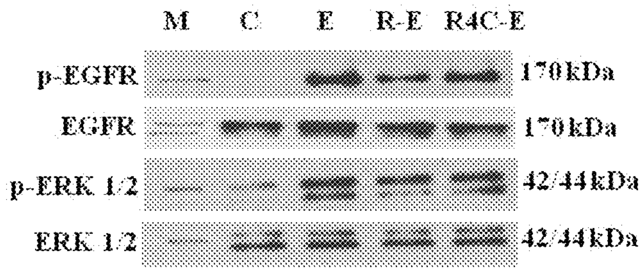
FIGS. 5A-5B show that "RGD-EGF and RGD4C-EGF" or "RGD-VEGF and RGD4C-VEGF" can activate the downstream signaling pathways of EGRF or VEGFR. The EGF or VEGF part of the dual targeting drug carrier of the present invention still remains the original biologically activity. The EGF and VEGF on the dual targeting drug carriers of the present invention still retained their original properties.
Figure 5B:
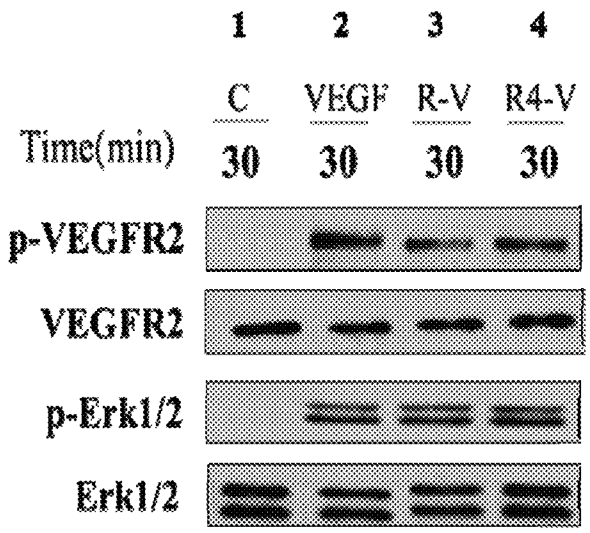

According to FIG. 5, MDA-MB468 cells expressing EGFR were co-cultured with RGD-EGF and RGD4C-EGF, or HUVEC cells expressing VEGFR1 and VEGFR2 were co-cultured with RGD-VEGF and RGD4C-VEGF. The downstream signal molecules of EGFR (FIG. 5A) or VEGFR (FIG. 5B) were analyzed. The downstream signal pathway of EGFR or VEGFR could be activated by "RGD-EGF and RGD4C-EGF" and "RGD-VEGF and RGD4C-VEGF", respectively. The results indicated that the dual targeting molecules can not only bind to biomarker, such as large peptide (e.g., EGF or VEGF), but also remain the original biological activity.

EXAMPLE 7

Figure 6:
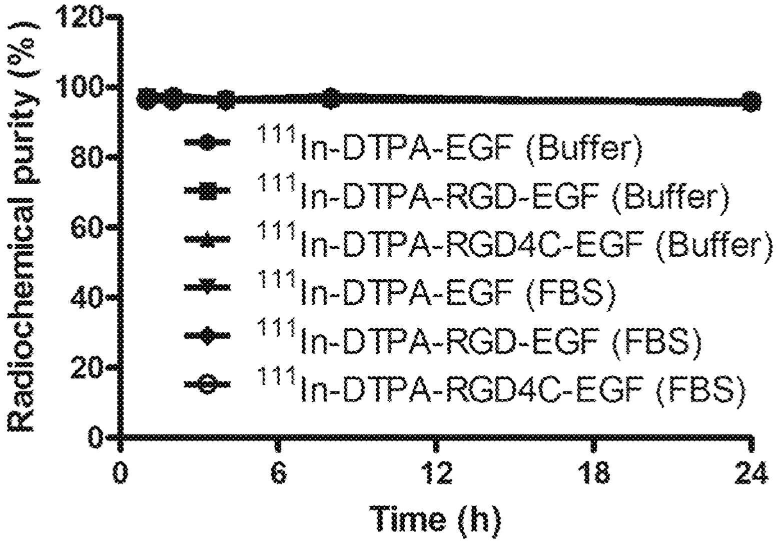
FIG. 6 is a graph showing the stability of the radio-labeled fusion protein in 4-(2-hydroxyethyl)-1-piperazineethanesulfonic acid (HEPES) buffer (4° C.) and serum (37° C.). After 24 hours, the radiochemical purity was higher than 90% in HEPES buffer at 4° C. or fetal bovine serum at 37° C. The result indicated that the 111In labeled fusion protein is very stable in serum.

Preparation of Radio-Targeting Fusion Proteins 2-(4-isothiocyanatobenzyl)-diethylenetriaminepentaacetic acid (p-SCN-Bn-DTPA) was dissolved in 4-(2-hydroxyethyl)-1-piperazineethanesulfonic acid (HEPES) buffer. The RGD-EGF or RGD4C-EGF targeting fusion protein was treated with the p-SCN-Bn-DTPA solution at room temperature for 1 hour. The unreacted small molecules were removed by gel filtration chromatography using Sephadax G25 to obtain the radio-targeting precursor proteins, DTPA-RGD-EGF and DTPA-RGD4C-EGF. HEPES buffer and radio-molecules (111InCl3, 67GaCl3, 90YCl3, or 177LuCl3) was added to the DTPA fusion protein solution and cultured at room temperature for 1 hour. Excess amount of ethylenediaminetetraacetic acid (EDTA) was added to chelate the radiometal ions that were not bound to proteins. The fusion proteins were purified by membrane filtration methods and gel filtration chromatography to analyze the stability of radio-targeting fusion proteins in HEPES at 4° C. or serum at 37° C. FIG. 6 shows the stability of 111In-labeled targeting fusion proteins in HEPES at 4° C. or serum at 37° C. After 24 hours of incubation in HEPES buffer (4° C.) or serum (37° C.) for 24 hours, purity was still higher than 90%.

EXAMPLE 8

Cell Fluorescence Photography

Figure 7:
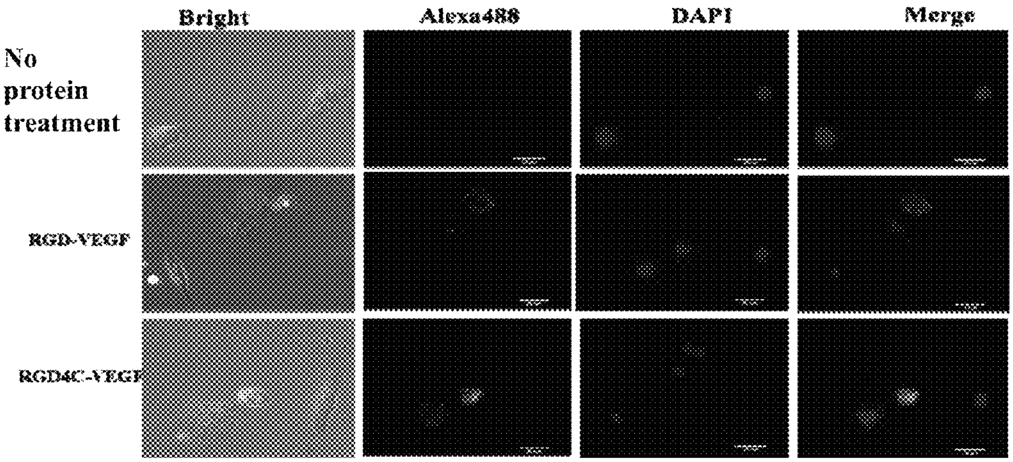
FIG. 7 is a fluorescence photomicrograph of cells. The fluorescent labeled RGD-VEGF and RGD4C-VEGF fusion protein could bind to cells.

Tumor or endothelial cells (2.5 $\times 10^5$ cells/well) were seeded into 12-well cell culture plates and cultured in a $CO_2$ incubator at 37° C. for 1 day. The attached cells were washed with 1 mL PBS buffer. VEGF, RGD-VEGF, and RGD4C-VEGF were added into different wells and incubated in an incubator at 37° C. with 5% $CO_2$ for 2 hours. Treated cells were washed three times with 0.5 mL PBS buffer and the FITC labeled anti-His tag antibodies were added for visualization. The fluorescence images were observed and acquired by fluorescent microscope with color CCD camera. Referring to FIG. 7, RGD-VEGF and RGD4C-VEGF targeting fusion proteins can bind to tumor and endothelial cells.

EXAMPLE 9

Figure 8:
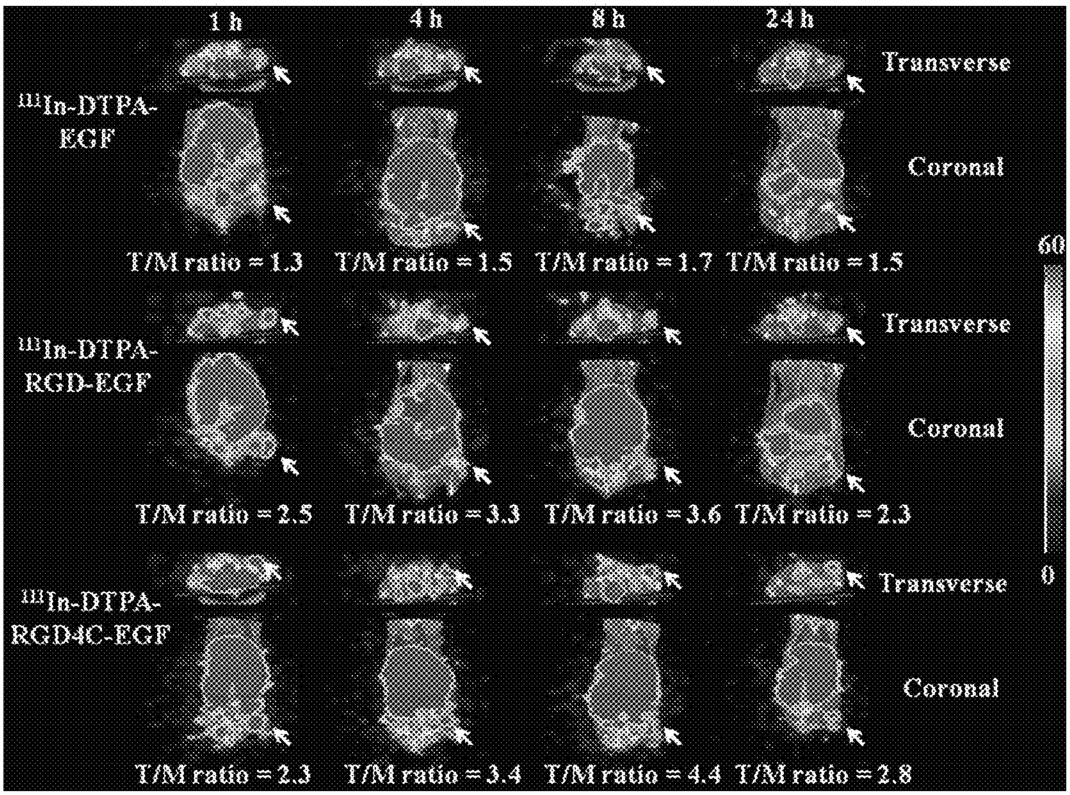
FIG. 8 is a single photon emission computed tomography (SPECT)/computed tomography (CT) image of radio-labeled fusion proteins. The U87MG xenografted nude mice are injected with 111In-DTPA-EGF, 111In-DTPA-RGD-EGF, or 111In-DTPA-RGD4C-EGF through tail vein. After 1, 4, 8, and 24 hours of tail vein injection, SPECT and CT scans were conducted. The results indicated that the tumor-specific accumulation (tumor to muscle accumulation ratio) is increased dependent upon elapsed time after injection. The tumor-specific accumulation is highest at 8 hours after injection. The tumor to muscle accumulation ratio was 4.4 in mice administered with 111In-DTPA-RGD4C-EGF, which is higher than that of mice administered with 111In-DTPA-EGF (accumulation ratio=1.7).

Single Photon Emission Computed Tomography (SPECT) and Computed Tomography (CT) Image of Radio-Labeled Fusion Protein Tumor-bearing nude mice (tumor size of 50-100 $mm^3$) were used in this Example. Mice were administered with 500 μL of radio-labeled targeting fusion proteins through tail vein. After 1, 4, 8, and 24 hours of tail vein injection, SPECT and CT scans were carried out. After radiography, the regions of interest (ROI) were selected to measure a tumor to muscle ratio and drugs accumulation in live mice. Referring to FIG. 8, U87MG tumor mice were injected with $^{111}$In-DTPA-EGF, $^{111}$In-DTPA-RGD-EGF, or $^{111}$In-DTPA-RGD4C-EGF through tail vein. After 1, 4, 8, and 24 hours of injection, SPECT and CT scans were conducted to analyze the accumulation ratio. The tumor-specific accumulation (accumulation ratio of tumor/muscle) of all targeting fusion proteins was increased dependent upon time. The ration reached highest at 8 hours after injection. At 8 hours after injection, the accumulation ratio of $^{111}$In-DTPA-RGD4C-EGF was 4.4, which was higher than that of $^{111}$In-DTPA-RGD-EGF (3.6) and $^{111}$1n-DTPA-EGF (1.7).

These results indicated that both RGD4C-EGF and RGD-EGF fusion proteins had dual targeting capability. The tumor-targeting capability of dual targeting fusion protein of the present invention was significantly better than single targeting EGF fusion protein. Additionally, the cyclic RGD peptide was superior in the integrin (αvβ3) binding than the linear RGD peptide.

What is claimed is:

1. A dual targeting drug carrier consisting of a first targeting molecule and a second targeting molecule, wherein the first targeting molecule is selected from the group consisting of Arg-Gly-Asp (RGD) and RGD4C, and the second targeting molecule is selected from the group consisting of epidermal growth factor (EGF) and vascular endothelial growth factor (VEGF), wherein the first targeting molecule and the second targeting molecule are selected from the group consisting of RGD-EGF (SEQ ID NO: 2), RGD4C-EGF (SEQ ID NO: 3), RGD-VEGF (SEQ ID NO: 7), and RGD4C-VEGF (SEQ ID NO: 8).

2. The dual targeting drug carrier according to claim 1, wherein the first and second targeting molecules specifically bind to tumor cells or vascular endothelial cells in tumor microenvironment.

3. A radio-labeled fusion protein, comprising the dual targeting drug carrier of claim 1 and a radioactive nuclide.

4. The radio-labeled fusion protein according to claim 3, wherein the dual targeting drug carrier is linked to the radioactive nuclide by a metal chelator.

5. The radio-labeled fusion protein according to claim 4, wherein the metal chelator is selected from a group consisting of DTPA, NOTA, DOTA, and derivate thereof.

* * * * *

SEQUENCE LISTING

```
<160> NUMBER OF SEQ ID NOS: 20

<210> SEQ ID NO 1
<211> LENGTH: 63
<212> TYPE: PRT
<213> ORGANISM: Artificial Sequence
<220> FEATURE:
<223> OTHER INFORMATION: EGF portein

<400> SEQUENCE: 1

Met Ala Asn Ser Asp Ser Glu Cys Pro Leu Ser His Asp Gly Tyr Cys
1               5                   10                  15

Leu His Asp Gly Val Cys Met Tyr Ile Glu Ala Leu Asp Lys Tyr Ala
            20                  25                  30

Cys Asn Cys Val Val Gly Tyr Ile Gly Glu Arg Cys Gln Tyr Arg Asp
        35                  40                  45

Leu Lys Trp Trp Glu Leu Arg Leu Glu His His His His His His
    50                  55                  60


<210> SEQ ID NO 2
<211> LENGTH: 66
<212> TYPE: PRT
<213> ORGANISM: Artificial Sequence
<220> FEATURE:
<223> OTHER INFORMATION: RGD-EGF protein

<400> SEQUENCE: 2

Met Ala Arg Gly Asp Asn Ser Asp Ser Glu Cys Pro Leu Ser His Asp
1               5                   10                  15

Gly Tyr Cys Leu His Asp Gly Val Cys Met Tyr Ile Glu Ala Leu Asp
            20                  25                  30

Lys Tyr Ala Cys Asn Cys Val Val Gly Tyr Ile Gly Glu Arg Cys Gln
        35                  40                  45

Tyr Arg Asp Leu Lys Trp Trp Glu Leu Arg Leu Glu His His His His
    50                  55                  60

His His
65


<210> SEQ ID NO 3
<211> LENGTH: 72
<212> TYPE: PRT
<213> ORGANISM: Artificial Sequence
<220> FEATURE:
<223> OTHER INFORMATION: RGD4C-RGF protein

<400> SEQUENCE: 3
```

-continued

```
Met Ala Cys Asp Cys Arg Gly Asp Cys Phe Cys Asn Ser Asp Ser Glu
1               5                   10                  15

Cys Pro Leu Ser His Asp Gly Tyr Cys Leu His Asp Gly Val Cys Met
            20                  25                  30

Tyr Ile Glu Ala Leu Asp Lys Tyr Ala Cys Asn Cys Val Val Gly Tyr
        35                  40                  45

Ile Gly Glu Arg Cys Gln Tyr Arg Asp Leu Lys Trp Trp Glu Leu Arg
    50                  55                  60

Leu Glu His His His His His His
65                  70


<210> SEQ ID NO 4
<211> LENGTH: 70
<212> TYPE: PRT
<213> ORGANISM: Artificial Sequence
<220> FEATURE:
<223> OTHER INFORMATION: YNGRT-EGF protein

<400> SEQUENCE: 4

Met Gly Tyr Asn Gly Arg Thr Gly Gly Asn Ser Asp Ser Glu Cys Pro
1               5                   10                  15

Leu Ser His Asp Gly Tyr Cys Leu His Asp Gly Val Cys Met Tyr Ile
            20                  25                  30

Glu Ala Leu Asp Lys Tyr Ala Cys Asn Cys Val Val Gly Tyr Ile Gly
        35                  40                  45

Glu Arg Cys Gln Tyr Arg Asp Leu Lys Trp Trp Glu Leu Arg Leu Glu
    50                  55                  60

His His His His His His
65                  70


<210> SEQ ID NO 5
<211> LENGTH: 70
<212> TYPE: PRT
<213> ORGANISM: Artificial Sequence
<220> FEATURE:
<223> OTHER INFORMATION: CNGRC-EGF protein

<400> SEQUENCE: 5

Met Gly Cys Asn Gly Arg Cys Gly Gly Asn Ser Asp Ser Glu Cys Pro
1               5                   10                  15

Leu Ser His Asp Gly Tyr Cys Leu His Asp Gly Val Cys Met Tyr Ile
            20                  25                  30

Glu Ala Leu Asp Lys Tyr Ala Cys Asn Cys Val Val Gly Tyr Ile Gly
        35                  40                  45

Glu Arg Cys Gln Tyr Arg Asp Leu Lys Trp Trp Glu Leu Arg Leu Glu
    50                  55                  60

His His His His His His
65                  70


<210> SEQ ID NO 6
<211> LENGTH: 131
<212> TYPE: PRT
<213> ORGANISM: Artificial Sequence
<220> FEATURE:
<223> OTHER INFORMATION: VEGF

<400> SEQUENCE: 6

Met Val Ala Pro Met Ala Glu Gly Gly Gly Gln Asn His His Glu Val
1               5                   10                  15
```

-continued

```
Val Lys Phe Met Asp Val Tyr Gln Arg Ser Tyr Cys His Pro Ile Glu
            20                  25                  30

Thr Leu Val Asp Ile Phe Gln Glu Tyr Pro Asp Glu Ile Glu Tyr Ile
        35                  40                  45

Phe Lys Pro Ser Cys Val Pro Leu Met Arg Cys Gly Gly Cys Cys Asn
    50                  55                  60

Asp Glu Gly Leu Glu Cys Val Pro Thr Glu Glu Ser Asn Ile Thr Met
65                  70                  75                  80

Gln Ile Met Arg Ile Lys Pro His Gln Gly Gln His Ile Gly Glu Met
                85                  90                  95

Ser Phe Leu Gln His Asn Lys Cys Glu Cys Arg Pro Lys Lys Asp Arg
            100                 105                 110

Ala Arg Gln Glu Lys Cys Asp Lys Pro Arg Arg Leu Glu His His His
        115                 120                 125

His His His
    130


<210> SEQ ID NO 7
<211> LENGTH: 134
<212> TYPE: PRT
<213> ORGANISM: Artificial Sequence
<220> FEATURE:
<223> OTHER INFORMATION: RGD-VEGF

<400> SEQUENCE: 7

Met Gly Arg Gly Asp Ala Pro Met Ala Glu Gly Gly Gly Gln Asn His
1               5                   10                  15

His Glu Val Val Lys Phe Met Asp Val Tyr Gln Arg Ser Tyr Cys His
            20                  25                  30

Pro Ile Glu Thr Leu Val Asp Ile Phe Gln Glu Tyr Pro Asp Glu Ile
        35                  40                  45

Glu Tyr Ile Phe Lys Pro Ser Cys Val Pro Leu Met Arg Cys Gly Gly
    50                  55                  60

Cys Cys Asn Asp Glu Gly Leu Glu Cys Val Pro Thr Glu Glu Ser Asn
65                  70                  75                  80

Ile Thr Met Gln Ile Met Arg Ile Lys Pro His Gln Gly Gln His Ile
                85                  90                  95

Gly Glu Met Ser Phe Leu Gln His Asn Lys Cys Glu Cys Arg Pro Lys
            100                 105                 110

Lys Asp Arg Ala Arg Gln Glu Lys Cys Asp Lys Pro Arg Arg Leu Glu
        115                 120                 125

His His His His His His
    130


<210> SEQ ID NO 8
<211> LENGTH: 140
<212> TYPE: PRT
<213> ORGANISM: Artificial Sequence
<220> FEATURE:
<223> OTHER INFORMATION: RGD4C-VEGF protein

<400> SEQUENCE: 8

Met Gly Cys Asp Cys Arg Gly Asp Cys Phe Cys Ala Pro Met Ala Glu
1               5                   10                  15

Gly Gly Gly Gln Asn His His Glu Val Val Lys Phe Met Asp Val Tyr
            20                  25                  30

Gln Arg Ser Tyr Cys His Pro Ile Glu Thr Leu Val Asp Ile Phe Gln
        35                  40                  45
```

```
Glu Tyr Pro Asp Glu Ile Glu Tyr Ile Phe Lys Pro Ser Cys Val Pro
    50                  55                  60

Leu Met Arg Cys Gly Gly Cys Cys Asn Asp Glu Gly Leu Glu Cys Val
65                  70                  75                  80

Pro Thr Glu Glu Ser Asn Ile Thr Met Gln Ile Met Arg Ile Lys Pro
                85                  90                  95

His Gln Gly Gln His Ile Gly Glu Met Ser Phe Leu Gln His Asn Lys
            100                 105                 110

Cys Glu Cys Arg Pro Lys Lys Asp Arg Ala Arg Gln Glu Lys Cys Asp
        115                 120                 125

Lys Pro Arg Arg Leu Glu His His His His His His
    130                 135                 140


<210> SEQ ID NO 9
<211> LENGTH: 138
<212> TYPE: PRT
<213> ORGANISM: Artificial Sequence
<220> FEATURE:
<223> OTHER INFORMATION: YNGRT-VEGF protein

<400> SEQUENCE: 9

Met Gly Tyr Asn Gly Arg Thr Gly Gly Ala Pro Met Ala Glu Gly Gly
1               5                   10                  15

Gly Gln Asn His His Glu Val Val Lys Phe Met Asp Val Tyr Gln Arg
            20                  25                  30

Ser Tyr Cys His Pro Ile Glu Thr Leu Val Asp Ile Phe Gln Glu Tyr
        35                  40                  45

Pro Asp Glu Ile Glu Tyr Ile Phe Lys Pro Ser Cys Val Pro Leu Met
    50                  55                  60

Arg Cys Gly Gly Cys Cys Asn Asp Glu Gly Leu Glu Cys Val Pro Thr
65                  70                  75                  80

Glu Glu Ser Asn Ile Thr Met Gln Ile Met Arg Ile Lys Pro His Gln
                85                  90                  95

Gly Gln His Ile Gly Glu Met Ser Phe Leu Gln His Asn Lys Cys Glu
            100                 105                 110

Cys Arg Pro Lys Lys Asp Arg Ala Arg Gln Glu Lys Cys Asp Lys Pro
        115                 120                 125

Arg Arg Leu Glu His His His His His His
    130                 135


<210> SEQ ID NO 10
<211> LENGTH: 138
<212> TYPE: PRT
<213> ORGANISM: Artificial Sequence
<220> FEATURE:
<223> OTHER INFORMATION: CNGRC-VEGF protein

<400> SEQUENCE: 10

Met Gly Cys Asn Gly Arg Cys Gly Gly Ala Pro Met Ala Glu Gly Gly
1               5                   10                  15

Gly Gln Asn His His Glu Val Val Lys Phe Met Asp Val Tyr Gln Arg
            20                  25                  30

Ser Tyr Cys His Pro Ile Glu Thr Leu Val Asp Ile Phe Gln Glu Tyr
        35                  40                  45

Pro Asp Glu Ile Glu Tyr Ile Phe Lys Pro Ser Cys Val Pro Leu Met
    50                  55                  60

Arg Cys Gly Gly Cys Cys Asn Asp Glu Gly Leu Glu Cys Val Pro Thr
```

```
65                  70                  75                  80

Glu Glu Ser Asn Ile Thr Met Gln Ile Met Arg Ile Lys Pro His Gln
                85                  90                  95

Gly Gln His Ile Gly Glu Met Ser Phe Leu Gln His Asn Lys Cys Glu
            100                 105                 110

Cys Arg Pro Lys Lys Asp Arg Ala Arg Gln Glu Lys Cys Asp Lys Pro
        115                 120                 125

Arg Arg Leu Glu His His His His His His
    130                 135
```

```
<210> SEQ ID NO 11
<211> LENGTH: 189
<212> TYPE: DNA
<213> ORGANISM: Artificial Sequence
<220> FEATURE:
<223> OTHER INFORMATION: EGF gene

<400> SEQUENCE: 11

atggcgaata gtgactctga atgtcccctg tcccacgatg ggtactgcct ccatgatggt      60

gtgtgcatgt atattgaagc attggacaag tatgcatgca actgtgttgt tggctacatc     120

ggggagcgat gtcagtaccg agacctgaag tggtgggaac tgcgtctcga gcaccaccac     180

caccaccac                                                             189


<210> SEQ ID NO 12
<211> LENGTH: 198
<212> TYPE: DNA
<213> ORGANISM: Artificial Sequence
<220> FEATURE:
<223> OTHER INFORMATION: RGD-EGF gene

<400> SEQUENCE: 12

atggcgagag gtgataatag tgactctgaa tgtcccctgt cccacgatgg gtactgcctc      60

catgatggtg tgtgcatgta tattgaagca ttggacaagt atgcatgcaa ctgtgttgtt     120

ggctacatcg gggagcgatg tcagtaccga gacctgaagt ggtgggaact gcgtctcgag     180

caccaccacc accaccac                                                   198


<210> SEQ ID NO 13
<211> LENGTH: 216
<212> TYPE: DNA
<213> ORGANISM: Artificial Sequence
<220> FEATURE:
<223> OTHER INFORMATION: RGD4C-EGF gene

<400> SEQUENCE: 13

atggcgtgcg actgccgcgg tgattgcttc tgtaatagtg actctgaatg tcccctgtcc      60

cacgatgggt actgcctcca tgatggtgtg tgcatgtata ttgaagcatt ggacaagtat     120

gcatgcaact gtgttgttgg ctacatcggg gagcgatgtc agtaccgaga cctgaagtgg     180

tgggaactgc gtctcgagca ccaccaccac caccac                               216


<210> SEQ ID NO 14
<211> LENGTH: 210
<212> TYPE: DNA
<213> ORGANISM: Artificial Sequence
<220> FEATURE:
<223> OTHER INFORMATION: YNGRT-EGF gene

<400> SEQUENCE: 14

atgggctaca acggtcgtac tggtggtaat agtgactctg aatgtcccct gtcccacgat      60
```

gggtactgcc tccatgatgg tgtgtgcatg tatattgaag cattggacaa gtatgcatgc 120
aactgtgttg ttggctacat cggggagcga tgtcagtacc gagacctgaa gtggtgggaa 180
ctgcgtctcg agcaccacca ccaccaccac 210

<210> SEQ ID NO 15
<211> LENGTH: 210
<212> TYPE: DNA
<213> ORGANISM: Artificial Sequence
<220> FEATURE:
<223> OTHER INFORMATION: CNGRC-EGF gene

<400> SEQUENCE: 15
atgggctgca acggtcgttg tggtggtaat agtgactctg aatgtcccct gtcccacgat 60
gggtactgcc tccatgatgg tgtgtgcatg tatattgaag cattggacaa gtatgcatgc 120
aactgtgttg ttggctacat cggggagcga tgtcagtacc gagacctgaa gtggtgggaa 180
ctgcgtctcg agcaccacca ccaccaccac 210

<210> SEQ ID NO 16
<211> LENGTH: 393
<212> TYPE: DNA
<213> ORGANISM: Artificial Sequence
<220> FEATURE:
<223> OTHER INFORMATION: VEGF gene

<400> SEQUENCE: 16
atggtagctc ctatggcaga aggaggaggg cagaatcatc acgaagtggt gaagttcatg 60
gatgtctatc agcgcagcta ctgccatcca atcgagaccc tggtggacat cttccaggag 120
taccctgatg agatcgagta catcttcaag ccatcctgtg tgcccctgat gcgatgcggg 180
ggctgctgca atgacgaggg cctggagtgt gtgcccactg aggagtccaa catcaccatg 240
cagattatgc ggatcaaacc tcaccaaggc cagcacatag gagagatgag cttcctacag 300
cacaacaaat gtgaatgcag accaaagaaa gatagagcaa gacaagaaaa atgtgacaag 360
ccgcgacgac tcgagcacca ccaccaccac cac 393

<210> SEQ ID NO 17
<211> LENGTH: 402
<212> TYPE: DNA
<213> ORGANISM: Artificial Sequence
<220> FEATURE:
<223> OTHER INFORMATION: RGD-VEGF gene

<400> SEQUENCE: 17
atgggtagag gtgatgctcc tatggcagaa ggaggagggc agaatcatca cgaagtggtg 60
aagttcatgg atgtctatca gcgcagctac tgccatccaa tcgagaccct ggtggacatc 120
ttccaggagt accctgatga gatcgagtac atcttcaagc catcctgtgt gcccctgatg 180
cgatgcgggg gctgctgcaa tgacgagggc ctggagtgtg tgcccactga ggagtccaac 240
atcaccatgc agattatgcg gatcaaacct caccaaggcc agcacatagg agagatgagc 300
ttcctacagc acaacaaatg tgaatgcaga ccaaagaaag atagagcaag acaagaaaaa 360
tgtgacaagc cgcgacgact cgagcaccac caccaccacc ac 402

<210> SEQ ID NO 18
<211> LENGTH: 420
<212> TYPE: DNA
<213> ORGANISM: Artificial Sequence
<220> FEATURE:

-continued

```
<223> OTHER INFORMATION: RGD4C-VEGF gene

<400> SEQUENCE: 18

atgggttgcg actgccgcgg tgattgcttc tgtgctccta tggcagaagg aggagggcag      60

aatcatcacg aagtggtgaa gttcatggat gtctatcagc gcagctactg ccatccaatc     120

gagaccctgg tggacatctt ccaggagtac cctgatgaga tcgagtacat cttcaagcca     180

tcctgtgtgc ccctgatgcg atgcgggggc tgctgcaatg acgagggcct ggagtgtgtg     240

cccactgagg agtccaacat caccatgcag attatgcgga tcaaacctca ccaaggccag     300

cacataggag agatgagctt cctacagcac aacaaatgtg aatgcagacc aaagaaagat     360

agagcaagac aagaaaaatg tgacaagccg cgacgactcg agcaccacca ccaccaccac     420


<210> SEQ ID NO 19
<211> LENGTH: 414
<212> TYPE: DNA
<213> ORGANISM: Artificial Sequence
<220> FEATURE:
<223> OTHER INFORMATION: YNGRT-VEGF gene

<400> SEQUENCE: 19

atgggttaca acggtcgtac tggtggtgct cctatggcag aaggaggagg gcagaatcat      60

cacgaagtgg tgaagttcat ggatgtctat cagcgcagct actgccatcc aatcgagacc     120

ctggtggaca tcttccagga gtaccctgat gagatcgagt acatcttcaa gccatcctgt     180

gtgcccctga tgcgatgcgg gggctgctgc aatgacgagg gcctggagtg tgtgcccact     240

gaggagtcca acatcaccat gcagattatg cggatcaaac ctcaccaagg ccagcacata     300

ggagagatga gcttcctaca gcacaacaaa tgtgaatgca gaccaaagaa agatagagca     360

agacaagaaa aatgtgacaa gccgcgacga ctcgagcacc accaccacca ccac           414


<210> SEQ ID NO 20
<211> LENGTH: 391
<212> TYPE: DNA
<213> ORGANISM: Artificial Sequence
<220> FEATURE:
<223> OTHER INFORMATION: CNGRC-VEGF gene

<400> SEQUENCE: 20

atgggttgca acggtcgttg tggtggtgct cctatggcag aaggaggagg gcagaatcat      60

cacgaagtgg tgaagttcat ggatgtctat cagcgcagct actgccatcc aatcgagacc     120

ctggtggaca tcttccagga gtaccctgat gagatcgagt acatcttcaa gccatcctgt     180

gtgcccctga tgcgatgcgg gggctgctgc aatgacgagg gcctggagtg tgtgcccact     240

gaggagtcca acatcaccat gcagattatg cggatcaaac ctcaccaagg ccagcacata     300

ggagagatga gcttcctaca gcacaacaaa tgtgaatgca gaccaaagaa agatagagca     360

agacaagaaa aatgtgacaa gccgcgacga c                                    391
```